United States Patent
Oldham et al.

(10) Patent No.: US 7,199,357 B1
(45) Date of Patent: *Apr. 3, 2007

(54) IMAGE ENHANCEMENT BY SUB-PIXEL IMAGING

(75) Inventors: Mark F. Oldham, Los Gatos, CA (US); Austin B. Tomaney, San Francisco, CA (US)

(73) Assignee: Applera Corporation, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/456,495

(22) Filed: Jul. 10, 2006

Related U.S. Application Data (63) Continuation of application No. 10/660,460, filed on Sep. 11, 2003, now Pat. No. 7,075,059.

(51) Int. Cl.
*H01J 3/14* (2006.01)
*H01J 40/14* (2006.01)
*H01J 5/16* (2006.01)
*H01L 27/00* (2006.01)
*G01N 15/06* (2006.01)

(52) U.S. Cl. .................. 250/234; 250/208.1; 250/573; 356/237.4

(58) Field of Classification Search ............. 250/208.1, 250/234–236, 573; 382/145, 149; 356/237.4, 356/237.5
See application file for complete search history.

(56) References Cited

U.S. PATENT DOCUMENTS 7,075,059 B2 * 7/2006 Oldham et al. ............. 250/234
2004/0113050 A1 6/2004 Olszak et al.

OTHER PUBLICATIONS

R.N. Hook, A.S. Fruchter, "Dithering, Sampling and Image Reconstruction", ASP Conf. Ser., vol. 216, Astronomical Data Analysis Software and Systems IX, eds. N. Manset, C. Veillet, D. Crabtree (San Francisco: ASP), 521, 2000.

* cited by examiner

*Primary Examiner*—Stephone B. Allen
*Assistant Examiner*—Patrick J. Lee
(74) *Attorney, Agent, or Firm*—Knobbe, Martens, Olson & Bear LLP (57) ABSTRACT

Methods and apparatus for improving the resolution of an electronic imaging device having an array of pixels. Sub-pixel dimension movements between an object and the array of pixels are made, and an image is formed at each position. Resulting shifted images are combined to yield an effective resolution corresponding to an array having smaller pixels. Such methods and apparatus allow optical systems with existing pixel devices to form effective images of smaller feature sizes.

25 Claims, 10 Drawing Sheets

IMAGE ENHANCEMENT BY SUB-PIXEL IMAGING

RELATED APPLICATIONS

This application is a continuation of U.S. patent application Ser. No. 10/660,460 filed Sep. 11, 2003 now U.S. Pat. No. 7,075,059, entitled "IMAGE ENHANCEMENT BY SUB-PIXEL IMAGING" which is hereby incorporated in its entirety herein.

BACKGROUND

1. Field

The present teachings generally relate to the field of signal processing and more particularly, to a system and methods for detecting and resolving signals associated with a biological analysis platform.

2. Description of the Related Art

During biological analysis, such as nucleotide sequencing or microarray processing, photo-detectors such as charge coupled devices (CCD) may be used to detect signals arising from labeled samples or probe features responsive to selected target analytes. These signals may take the form of fluorescent or visible light emissions that are desirably analyzed to quantify observed light intensity arising from each labeled sample or probe feature and are subsequently resolved to quantitatively or qualitatively evaluate the presence of a target analyte within a sample.

Generally, the photo detector used in such a biological analysis comprises a segmented array of light-detecting elements or pixels. Each pixel's relative size is one factor that contributes to the achievable resolution of the detected image and as the image is magnified close to the order of pixel dimension various pixel effects may be observed which create difficulties in signal analysis. One common pixel effect appears as an array of squares at sharp edges in the image which may have the effect of reducing the resolution of the detected image. This pixel effect may also arise when acquiring signals from small point-like features, such as those found in microarray platforms where the feature shape and the information originating therefrom may be undesirably compromised as a result of imaging artifacts.

Consequently, there is an ongoing need for an improved approach in which photo-detectors are used to preserve the overall quality of optically detected images in biological analysis.

SUMMARY OF THE INVENTION

One aspect of the present teachings relates to a system for interrogating a sample using a probe array configured to be responsive to a plurality of particles. One or more identifiable signals arise from the probe array following interaction with the sample particles which may comprise labeled proteins, DNA, RNA, or other biomolecules. The sample composition is resolved, at least in part, by identifying the signals associated with constituent probe features of the array which generally reflect the amount or quantity of a particular particle type which interacts with the selected probe feature or element. The system comprises a platform that supports the probe array, and a segmented detector configured to detect at least a portion of the one or more identifiable signals associated with the constituent probe features of the array. Based on knowledge of the composition and position of each probe, feature, or element in the array, and the signal arising therefrom; this information may be used to identify the presence and type of particles contained within a selected sample. The segmented detector comprises a plurality of pixels having a specified dimension, with the segmented detector oriented with respect to the probe array such that the one or more identifiable signals associated with the constituent probes form an optical image of probe array at the segmented detector. The system further comprises a movement mechanism that provides a relative movement between the platform and the segmented detector. The relative movement includes a lateral movement that causes the optical image of the probe array to shift laterally with respect to a normal of the segmented detector. The movement mechanism is capable of such lateral movements in sub-pixel sized steps. The system further comprises a processor that induces a plurality of the sub-pixel sized lateral shifts in the image of the probe array with respect to the segmented detector. The identifiable signals detected at the various lateral positions of the image with respect to the segmented detector are combined to yield a composite signal associated with the multiplicity of images such that the composite signal improves the effective resolution of signal detection which may be better than the dimension of the pixel.

In certain embodiments, the movement mechanism comprises a movable stage coupled to the platform. The movable stage is configured to move such that the image moves laterally with respect to an optical axis at the segmented detector. The movable stage is capable of fine movements that cause the lateral movements of the image at a sub-pixel level.

In one embodiment, the pixel configuration of the segmented detector is represented by a generally square active area with two substantially perpendicular sides of the square area generally parallel to an X and Y axes of a two dimensional detector coordinate system. The sub-pixel movements of the image may comprise sub-pixel movements along the X and Y axes. In one embodiment, the magnitude of each sub-pixel movement along the X and Y axes is approximately an integer fraction of the side dimension of the square area. Such sub-pixel movements could be, for example, in ½, ⅓, ¼, ⅕, ⅙, ⅛ pixel dimension steps.

In certain embodiments, the platform comprises a bundle of fibers having their tips arranged generally in a planar manner. The tips of the fibers form the probe array and the diameter of each fiber defines a feature size to be resolved by the segmented detector. In one embodiment, the segmented detector comprises a CCD having a plurality of pixels shaped generally as squares. In one embodiment, the pixel square is dimensioned such that the side of the pixel square is greater than approximately ⅓ of the diameter of the fiber. In one embodiment, the pixel square side is approximately 21 μm long and the fiber diameter is approximately 50 μm.

In certain embodiments, the sub-pixel sized shifts of the image relative to the segmented detector allows a processor to estimate what a sub-pixel sized element might output based on the combination of the associated pixels that overlap with the location of the sub-pixel sized element. In one embodiment, the sub-pixel sized element is dimensioned according to the magnitudes of the sub-pixel sized shifts. The estimate of the sub-pixel element's output can be expressed as $$I = \frac{\sum_i d_i a_i w_i}{W},$$

where $$W = \sum_i a_i w_i,$$

$d_i$ represents the pixel output at the i-th position, $a_i$ represents the overlap fraction of the pixel at the i-th position with the sub-pixel element, and $w_i$ represents a weight parameter associated with the i-th position of the pixel. In one embodiment, the weight parameter $a_i$ associated with the i-th position of the pixel is user defined. In one embodiment, the weight parameter $a_i$ is assigned a constant value of 1/N where N is the number of pixel positions that overlap with the sub-pixel element.

Another aspect of the present teachings relates to a method for improving the effective resolution of an image of an array of biological probes positioned on an analysis platform. Each probe is configured to be responsive to a specific particle having unique identifying characteristics. When the array of probes is exposed to the sample, the probes generate an identifiable signal based on the interaction of the probes with specific particles within the sample based upon the unique identifying characteristics of the specific particle. The identifiable signals from the array of probes are captured by a plurality of pixels of a segmented detector so as to form the image of the array of probes. The method comprises inducing a plurality of relative motions between the image of the array of probes and the segmented detector. The method further comprises capturing the identifiable signals from the array of probes at a plurality of relative positions between the array of probes and the segmented detectors. The plurality of relative positions correspond to the plurality of relative motions. The method further comprises combining the captured identifiable signals associated with the plurality of relative positions so as to yield a combined image. The combined image has an effective resolution that is better than a dimension representative of the size of an element of the segmented detector.

In certain implementations, inducing the plurality of relative motions comprises causing the analysis platform to move such that the image of the array of probes moves laterally with respect to the optical axis of the segmented detector. In one implementation, the movement of the analysis platform causes the image to move by a step that is less than the dimension of the pixel of the segmented detector. In one implementation, the image movement step is an integer fraction of the pixel dimension. In one implementation, the pixel of the segmented detector has a generally square active area and two perpendicular sides of the square area are respectively generally parallel to X and Y axes of a two dimensional detector coordinate system. The image movement steps are along the X and Y axes.

In certain implementations, combining the captured identifiable signals comprises combining outputs of pixels that overlap with a selected area on the segmented detector when the pixels are at the plurality of relative positions with respect to the image. In one implementation, the selected area comprises an area that has sub-pixel dimensions. In one implementation, an output that could result from the sub-pixel sized selected area is estimated as $$I = \frac{\sum_i d_i a_i w_i}{W},$$

where $$W = \sum_i a_i w_i,$$

$d_i$ represents the pixel output at the i-th position, $a_i$ represents the overlap fraction of the pixel at the i-th position with the selected area, and $w_i$ represents a weight parameter associated with the i-th position of the pixel. In one implementation, the weight parameter $a_i$ associated with the i-th position of the pixel is user defined. In one implementation, the weight parameter $a_i$ is assigned a constant value of 1/N where N is the number of pixel positions that overlap with the selected area.

DETAILED DESCRIPTION OF THE CERTAIN EMBODIMENTS

These and other aspects, advantages, and novel features of the present teachings will become apparent upon reading the following detailed description and upon reference to the accompanying drawings. In the drawings, similar elements have similar reference numerals.

Figure 1A:
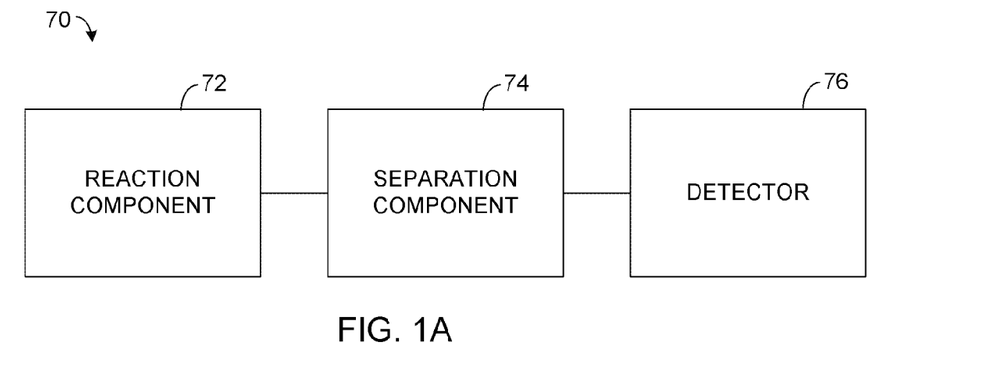
FIG. 1A illustrates a functional block diagram of a system adapted to measure components associated with biological related processes.

FIG. 1A illustrates an exemplary schematic diagram for a biological analyzer 70 capable of sequence determination or fragment analysis for nucleic acid samples. In various embodiments, the analyzer 70 may comprise one or more components or devices that are used for labeling and identification of the sample and may provide means for performing automated sequence analysis. The various components of the analyzer 70, described in greater detail hereinbelow, may comprise separate components or a singular integrated system. The present teachings may be applied to both automatic and semi-automatic sequence analysis systems as well as to methodologies wherein some of the sequence analysis operations are manually performed. Additionally, the methods described herein may be applied to other biological analysis platforms to improve the overall quality of the analysis In various embodiments, the methods and systems of the present teachings may be applied to numerous different types and classes of photo and signal detection methodologies and are not necessarily limited to CCD based detectors. Additionally, although the present teachings are described in various embodiments in the context of sequence analysis, these methods may be readily adapted to other devices/instrumentation and used for purposes other than biological analysis.

It will also be appreciated that the methods and systems of the present teachings may be applied to photo-detectors in general for a variety of applications, some of which are listed as examples above. Photo-detectors in general convert incident photons to electrical signals, and may include, by way example, CCDs, photomultipliers, or semiconductor based devices such as photo-diodes.

In the context of sequence analysis, the exemplary sequence analyzer 70 may comprise a reaction component 72 wherein amplification or reaction sequencing (for example, through label or marker incorporation by polymerase chain reaction) of various constituent molecules contained in the sample is performed. Using these amplification techniques, a label or tag, such as a fluorescent or radioactive dideoxy-nucleotide may be introduced into the sample constituents resulting in the production of a collection of nucleotide fragments of varying sequence lengths. Additionally, one or more labels or tags may be used during the amplification step to generate distinguishable fragment populations for each base/nucleotide to be subsequently identified. Following amplification, the labeled fragments may then be subjected to a separation operation using a separation component 74. In one aspect, the separation component 74 comprises a gel-based or capillary electrophoresis apparatus which resolves the fragments into substantially discrete populations. Using this approach, electrical current may be passed through the labeled sample fragments which have been loaded into a separation matrix (e.g. polyacrylamide or agarose gel). The application of an electrical current results in the migration of the sample through the matrix. As the sample migration progresses, the labeled fragments are separated and passed through a detector 76 wherein resolution of the labeled fragments is performed.

In one aspect, the detector 76 may identify various sizes or differential compositions for the fragments based on the presence of the incorporated label or tag. In one exemplary embodiment, fragment detection may be performed by generation of a detectable signal produced by a fluorescent label that is excited by a laser tuned to the label's absorption wavelength. Energy absorbed by the label results in a fluorescence emission that corresponds to a signal measured for each fragment. By keeping track of the order of fluorescent signal appearance along with the type of label incorporated into the fragment, the sequence of the sample can be discerned. A more detailed explanation of the sequencing process is provided in commonly assigned U.S. Pat. No. 6,040,586, entitled "Method and System for Velocity-Normalized Position-Based Scanning" which is hereby incorporated by reference in its entirety.

Figure 1B:
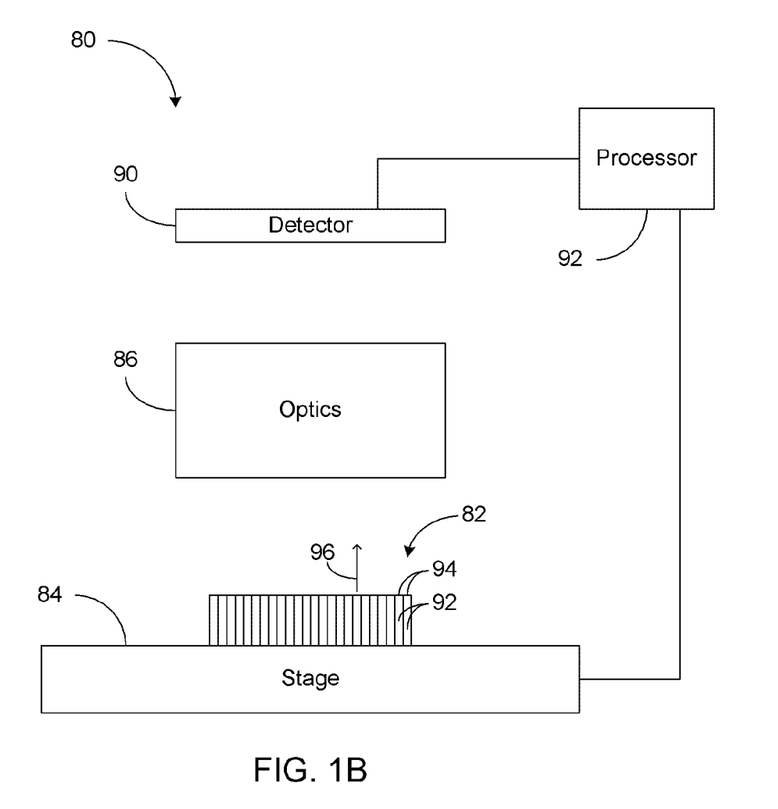
FIG. 1B illustrates a block diagram of an exemplary biological analysis system having an array-type biological sample platform that forms an optical image on a detector.

FIG. 1B illustrates exemplary components of an analyzer 80 configured to acquire signals associated with a biological sample located at a sample platform 82. The exemplary sample platform 82 comprises a plurality of fibers 92 arranged in a specified bundle such that tips 94 form an array of substrates onto which specified fragments adhere to. In certain embodiments, the fragments may be tagged with label molecules that emit known wavelength light when excited by an excitation energy such as a laser. The exemplary emitted light is depicted as an arrow 96. The fragment laden substrate tips may emit light at different intensity and/or wavelength. By measuring the emitted light from a given substrate tip, one can determine the presence and relative concentration of the fragment at that tip.

The signals from the biological sample reach a segmented detector 90 via an optical element 86. In certain embodiments, the optical element 86 may comprise one or more lenses adapted to direct the signals from the biological sample to the segmented detector 90 in a desired manner. In other embodiments, the optical element 86 may comprise a diffraction device that causes the signals from the biological sample to undergo diffraction so as to permit a spectroscopic analysis by the segmented detector 90.

In various embodiments, the optical element 86 directs the signals to the segmented detector 90 with an optical resolution that is finer than the resolving capability of the segmented detector. Thus in such systems, the resolving capability of the segmented detector may be the limiting factor in determining the achievable resolution of the analyzer.

In many segmented detectors, the resolving capability is determined by the size and/or spacing of the pixels. In certain applications, the pixels may be sized such that a signal from some feature on the biological sample, delivered to the detector 90 via the optical element 86, cannot be fully resolved. In such situations, a point or a sharp edge may end up appearing as a one or a series of pixel shapes (typically squares). In other applications where closely spaced sample features emitting light, the detector may not be able to separate out the light from one feature from that of another nearby feature. That is, a peak associated with one feature may not be identified distinctly from that of another feature.

As shown in FIG. 1B, the analyzer further comprises a processor 92 that receives the detected signals from the segmented detector 90. The processor may also be functionally connected to the stage 84. One aspect of the present teachings relates to the processor 92 causing a relative motion between the sample platform 82 and the detector to yield a plurality of detected signals that can be combined to yield an improved resolution better than that of the aforementioned limiting resolution determined solely by the pixel size. Various methods of achieving such improved resolution are described below in greater detail.

In general, the processor 92 may further be configured to operate in conjunction with one or more processors. The processor's components may include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables. Furthermore, the processor 92 may output a processed signal or analysis results to other devices or instrumentation where further processing may take place.

In various embodiments, some of the information that may be determined through signal (from feature) resolution and peak identification may include determination of the relative abundance or quantity of each fragment population. Evaluation of the signals may further be used to determine the sequence or composition of the sample using various known base sequence resolution techniques. It will further be appreciated by one of skill in the art that the exemplified signal distribution may represent one or more nucleic acid fragments for which the relative abundance of each fragment may be evaluated based, in part, upon the determination of the relative area of an associated peak in the signal distribution. The present teachings may therefore be integrated into existing analysis approaches to facilitate peak evaluation and subsequent integration operations typically associated with sequence analysis.

Figure 2A:
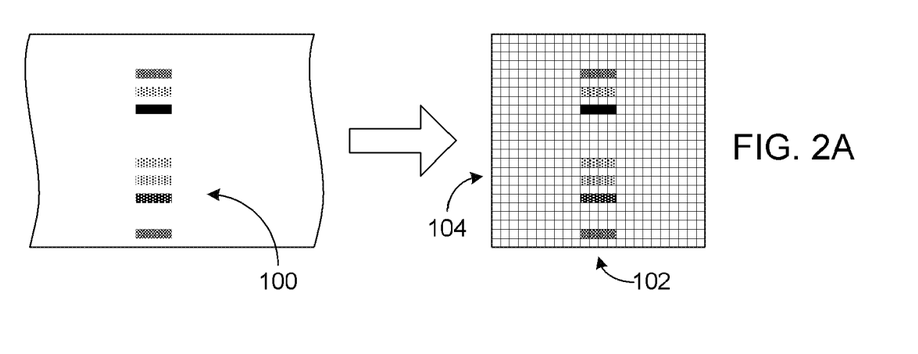
FIGS. 2A–C illustrate exemplary biological sample platforms and their corresponding images formed on segmented detectors.
Figure 2B:
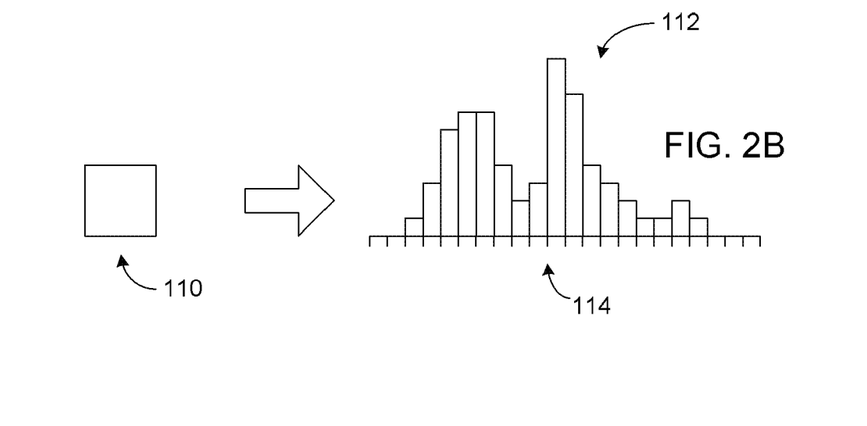
Figure 2C:
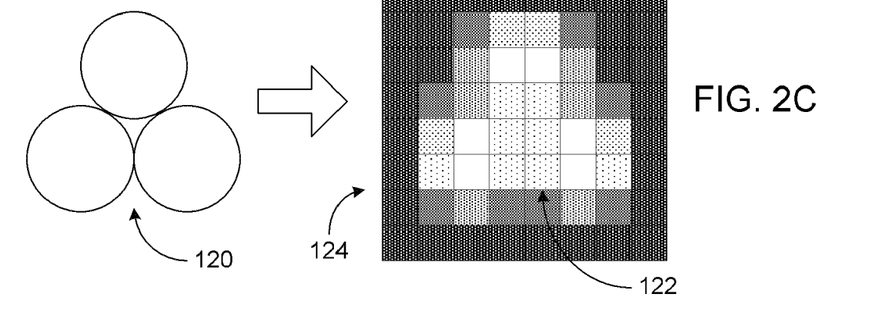

FIGS. 2A–C illustrate some of the possible biological analysis applications where the present teachings may be applied to provide the improved effective resolution of the segmented detectors. FIG. 2A illustrates an exemplary electrophoresis migration type sample 100 that forms a band-like emission bands depending on the relative concentrations of various labeled fragments. Such an emission band pattern may be imaged on a segmented detector 104 as a detected pattern 102. The various bands are depicted to emit the signals at different intensities.

FIG. 2B illustrates an exemplary biological sample 110 that emits a signal that undergoes a spectral separation to yield a wavelength-dependent intensity distribution 112 imaged on a segmented detector 114. In such a detected image, the dimension of the pixel may determine the bin size of a histogram that represents the distribution 112.

FIG. 2C illustrates an exemplary group of fiber tips 120 representative of a portion of a micro array type sample. Emissions from the fiber tips 120 are imaged on an exemplary segmented detector 124 as a detected pattern 122. The exemplary fiber tips 120 are depicted to emit signals with similar intensities for the purpose of description, but it will be understood that the fiber tips may emit differently depending on the concentrations of particular fragments attached thereto.

In the exemplary biological samples of FIGS. 2A–C, the quality of the resulting detected images depend to some degree on the dimension of the pixels of the respective detectors. Generally, one would like a detector to be able to resolve each emitting sample element (such as a fiber tip of FIG. 2C) as much as possible to accurately ascertain the amount of light being emitted therefrom. In certain configurations of segmented detectors, such as that in FIG. 2C, the pixel dimension relative to the sample feature size (fiber diameter) may be large enough such that the sample features are not resolved well.

As is generally known, an image formed on a segmented detector such as a CCD may be undersampled if the pixel dimension is too large relative to the image dimension. Undersampling may result in processed images having rectangular "graininess." The image dimension is frequently expressed as "full width at half-max" (FWHM) for images whose intensity profile can be approximated as being Gaussian. Generally, if the FWHM of the image covers more than two or more pixels, the image is considered to be well sampled. Thus, the effectively smaller pixels achieved by the sub-pixel relative movements between the detector and the image as described herein allow relatively small dimensioned images to be "well sampled" by appropriately selecting the sub-pixel step sizes.

Figure 3A:
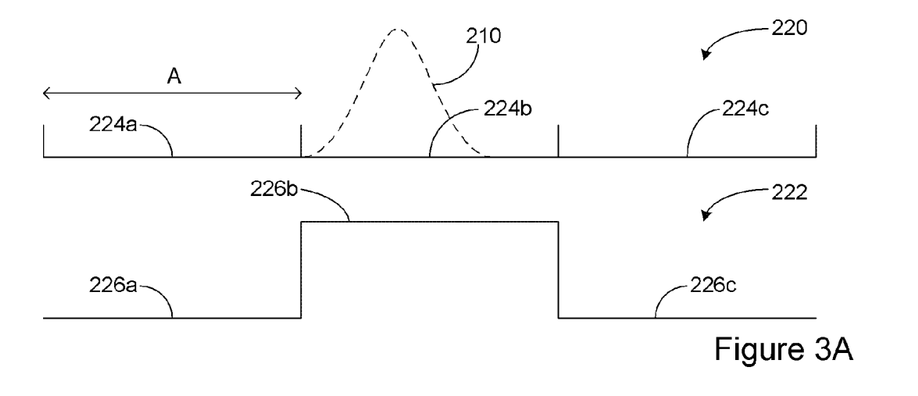
FIGS. 3A–C illustrate a mechanism by which smaller sized pixels can better resolve a selected sized feature.
Figure 3B:
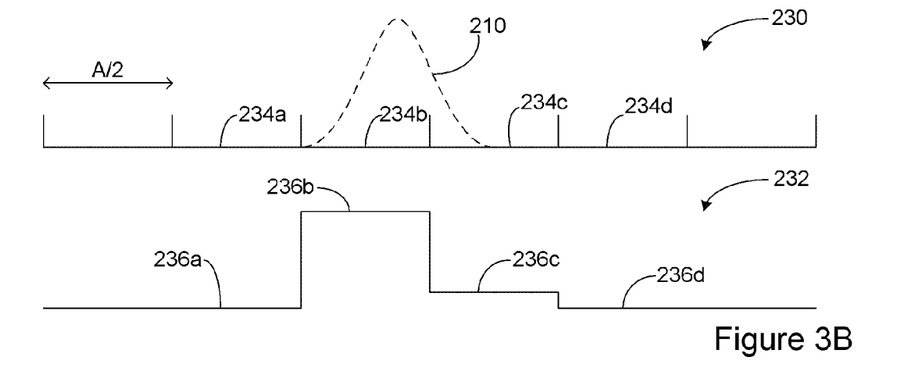
Figure 3C:
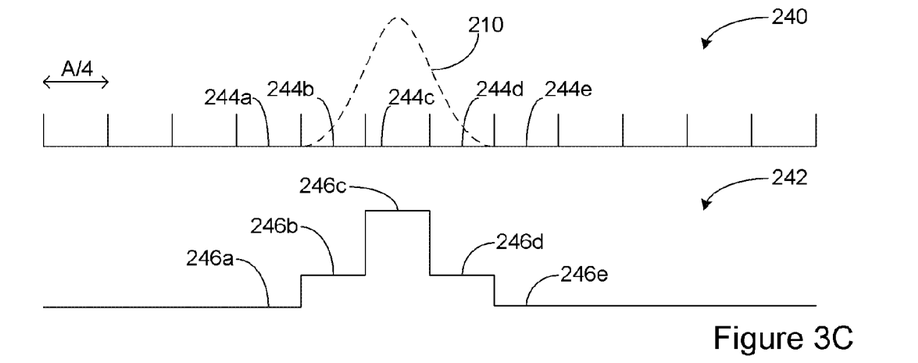

FIGS. 3A–C illustrate how a smaller pixel can better resolve an image 210 (of a feature) compared to a larger pixel. An exemplary first segmentation 220 comprises a plurality of pixels 224 having a dimension of A. An exemplary second segmentation 230 comprises a plurality of pixels 234 having a dimension of A/2. An exemplary third segmentation 240 comprises a plurality of pixels 244 having a dimension of A/4. It will be understood that the dimensions A/2 and A/4 are arbitrary and exemplary choices for descriptive purpose, and are not meant in any way to limit the scope of the present teachings. Other dimensions less than A may be used without departing from the spirit of the present teachings.

The image 210 overlapped on the first segmentation 220 shows that substantially all of the image 210 falls on the pixel 224$b$. Consequently, a resulting first segmentation output 222 comprises a step function, wherein output portions 226$a$, and 226$c$ correspond to backgrounds from the pixels 224$a$ and 224$c$, respectively, and output portion 226$b$ corresponds to the background plus the image signal from the pixel 224$b$. Such output can be considered to be representative of undersampling of the image 210. While such a resolution of the feature may suffice for an intensity measurement (assuming that the peak 210 is generally isolated from other peaks), the output from the first segmentation 220 offers little information about the peak's shape and precise location.

The image 210 overlapped on the second segmentation 230 shows that substantially all of the image 210 falls on the pixels 234$b$ and 234$c$. Consequently, a resulting second segmentation output 232 comprises background level signals from pixels other than 234$b$ and 234$c$. The pixel 234$b$ outputs a signal that is larger than that from the pixel 234$c$ since more of the image falls on the pixel 234$b$. Such output can also be considered to undersample the image 210.

The image 210 overlapped on the third segmentation 240 shows that substantially all of the image 210 falls on the pixels 244$b$, $c$, and $d$. Consequently, a resulting third segmentation output 242 comprises background level signals from pixels other than 244$b$–$d$. The pixels 244$b$–$d$ output signals that are proportional to fractions of the image 210 falling thereon. Although such output can also be considered as being undersampled according to the previously described rule (2–3 pixels covering FWHM), one can see that the output 242 begins to resemble the image 210.

It will be appreciated that the segmentation size with respect to the "original" (224 in FIG. 3A) size may take on any value, so long as it is smaller than the original size A. Thus, the segmentation size smaller than A/4 of FIG. 3C, such as A/6, may provide "well-sampled" criteria suitable for the exemplary image 210.

Figure 4:
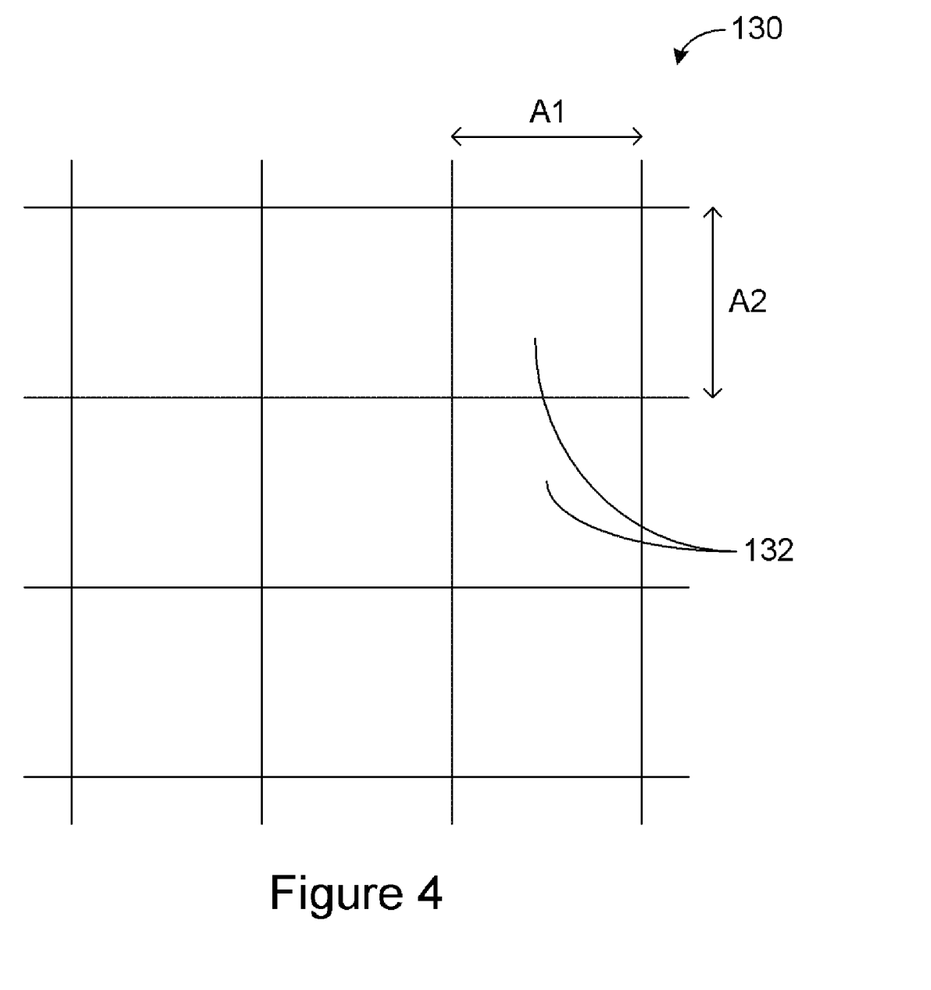
FIG. 4 illustrates an exemplary pixel array found in a segmented detector such as a charged coupled device (CCD)

FIG. 4 now illustrates a portion of a two dimensional segmented detector whose outputs can be combined in a manner described below to yield an improved effective resolution. In certain embodiments, a segmented detector 130 comprises a plurality of photo-sensitive elements (pixels) 132. In the description of the present teachings herein, the detector 130 and the elements 132 may be interchangeably referred to as CCD and pixels respectively. It will be understood, however, that such usage is not intended to limit the scope of the present teachings in any manner. Thus, the technique disclosed herein may be utilized in other types of segmented detectors without departing from the spirit of the present teachings.

Figure 5A:
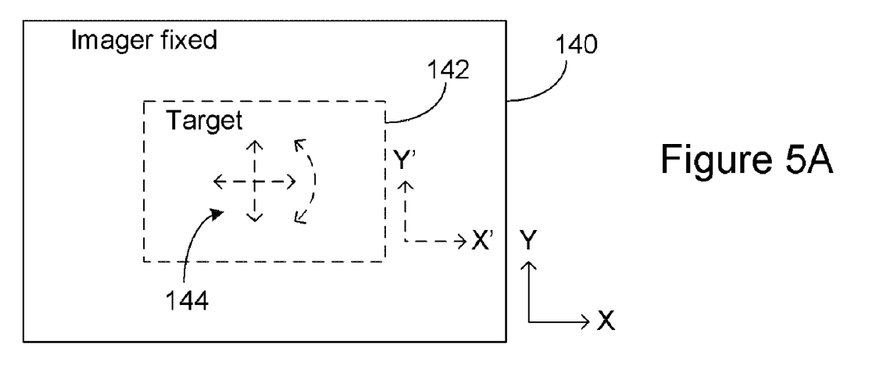
FIGS. 5A–C illustrate various possible relative movements between the biological sample platform and the segmented detector to allow improvement in the resolution of the signals obtained by the segmented detector.
Figure 5B:
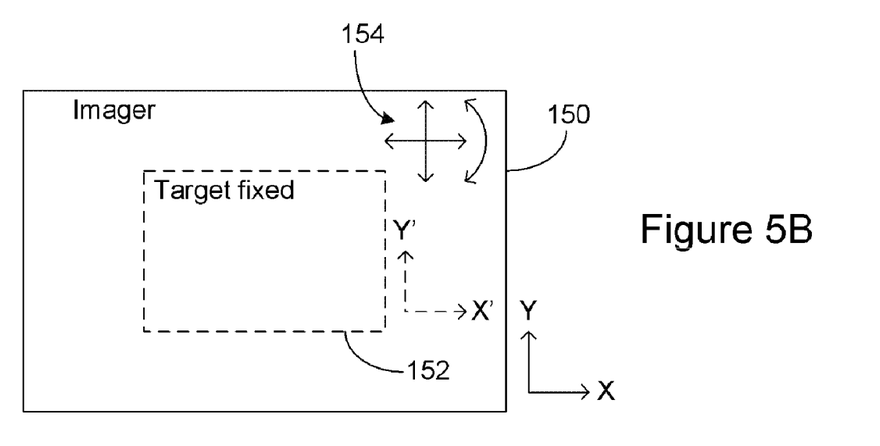
Figure 5C:
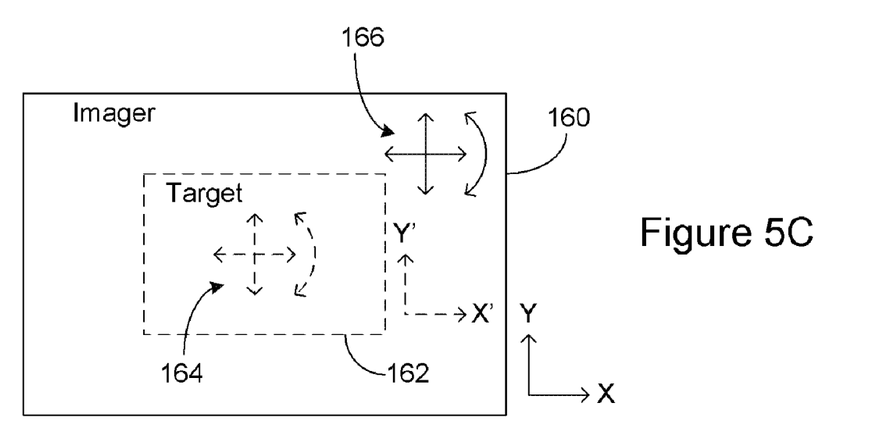

Various possible lateral movements are illustrated in FIGS. 5A–C. The unprimed coordinate system represents various detectors (also referred to as imagers herein), and the primed coordinate system represents various biological sample platforms (also referred herein as a target). FIG. 5A illustrates one possible embodiment having a target 142 moving with respect to an imager 140. The imager 140 is fixed and the target 142 moves laterally along X'-Y' directions and/or rotates about the Z' axis as indicated by arrows 144. FIG. 5B illustrates another possible embodiment having an imager 150 moving with respect to a target 152. The target 152 is fixed and the imager 150 moves laterally along X-Y directions and/or rotates about the Z axis as indicated by arrows 154. FIG. 5C illustrates yet another possible embodiment having a target 162 moving with respect to an imager 160. Both the target 162 and the imager 160 are movable with respect to each other and with respect to some optical system frame of reference. The target 162 moves laterally X'-Y' directions and/or rotates about the Z' axis as indicated by arrows 164. The imager 160 moves laterally along X-Y directions and/or rotates about the Z axis as indicated by arrows 166. Thus, it will be appreciated that various target-imager relative movements may be utilized to achieve image enhancements described herein without departing from the spirit of the present teachings.

Figure 6A:
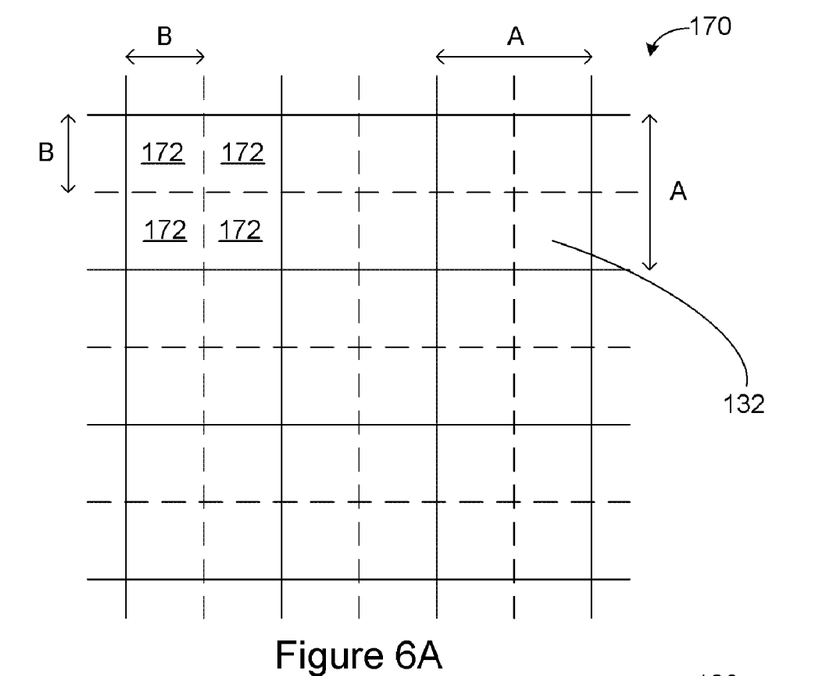
FIGS. 6A–B illustrate the mechanism by which sub-pixel movements between the biological sample platform and the segmented detector can facilitate formation of arrays having effectively smaller pixels.
Figure 6B:
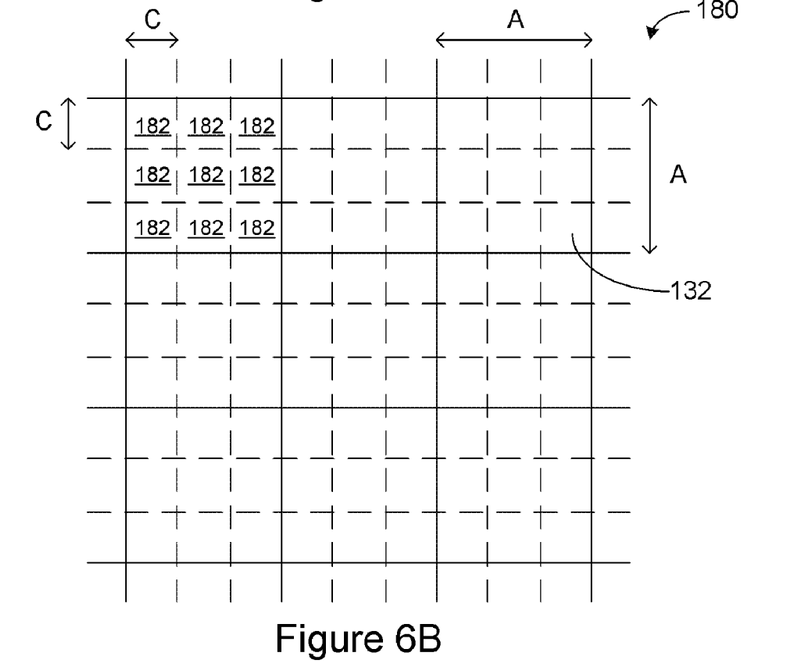

The relative movements achieved in the foregoing manner may be configured for sub-pixel step relative movements. In certain embodiments, images of the target at each of the sub-pixel steps may be combined, in manners described below, to yield a reconstructed image having an effective resolution comparable to the sub-pixel step dimension. As examples, FIGS. 6A and B illustrate effective pixels achieved by the sub-pixel movements. In FIG. 6A, a detector 170 comprises a plurality of pixels 132, with each pixel 132 having dimensions of A×A. The target-detector relative movement comprises half-pixel steps laterally such that each pixel 132 becomes divides into four effective pixels having dimensions of B×B, where B is approximately half of A.

Similarly in FIG. 6B, a detector 180 may be configured to allow relative lateral movements (between the target and the detector 180) in third-pixel steps. Such movements yield a division of the pixel 132 into nine effective pixels having dimensions of C×C, where C is approximately third of A.

It will be appreciated that the sub-pixel movements illustrated in FIGS. 6A–B are exemplary, and in no way intended to limit the scope of the present teachings. The sub-pixel movement may comprise any step movements where the step size is less than the dimension of the pixel. The pixel dimension may be integral multiple of the step size, but is not a requirement of the present teachings, so long as the step movements can be achieved in an accurate manner. Furthermore, certain embodiments may be configured to allow the step sizes to vary to suit different applications. For example, such embodiments may switch between the half-pixel and third-pixel step movement configurations illustrated in FIGS. 6A–B (as well as other step movements).

Figure 7:
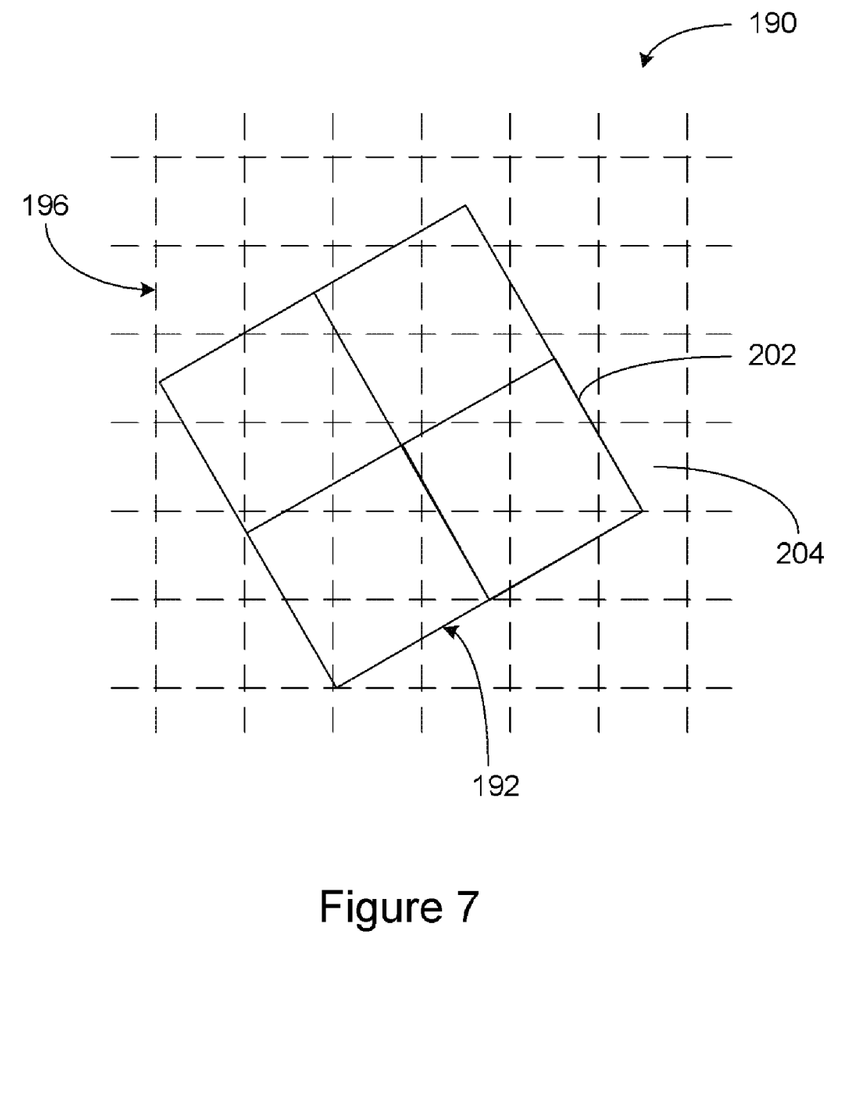
FIG. 7 illustrates generalized relative movements between the biological sample platform and the segmented detector, including a relative rotational movement.

The sub-pixel movements need not be restricted to the X-Y directions. In certain embodiments, as illustrated in FIG. 7, the target's orientation relative to the detector may be rotated and/or translated so as to yield a generalized mapping 190 between a pixel space 192 (represented by four pixels 202) and a sub-pixel space 196 (represented by sub-pixels 204).

Figure 8:
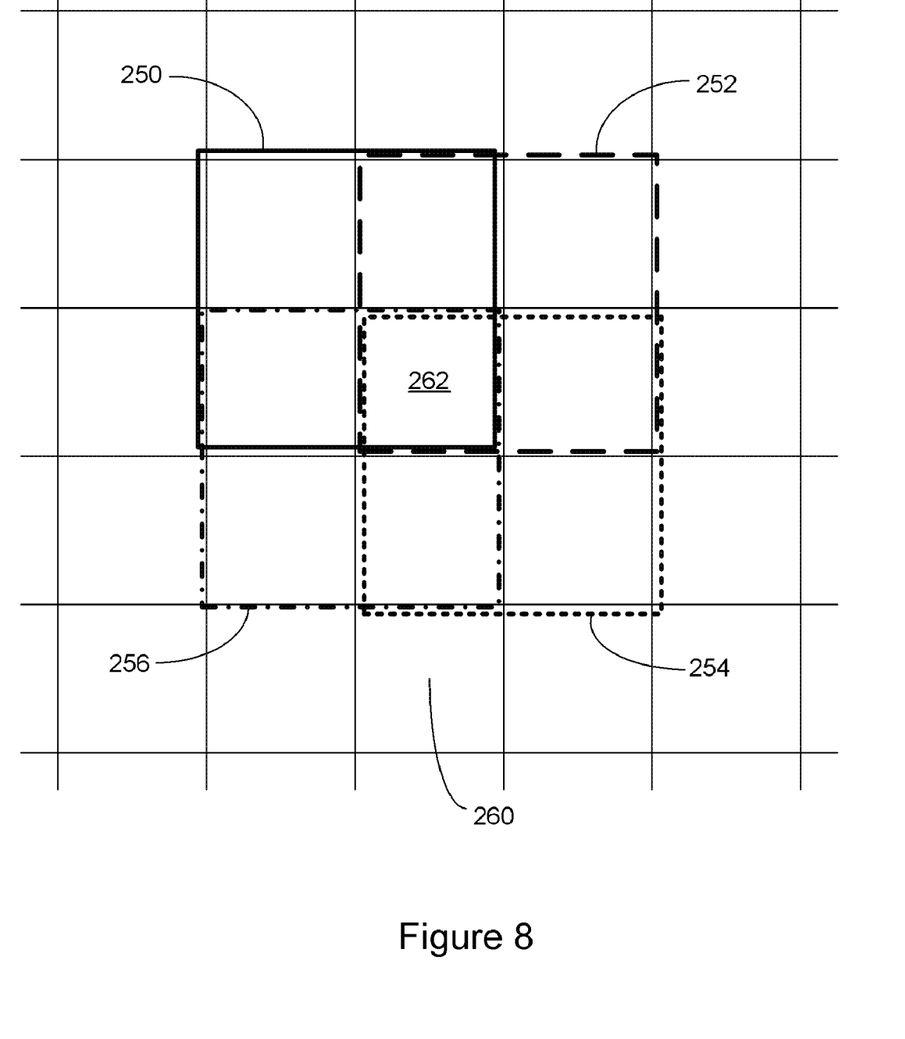
FIG. 8 illustrates an exemplary sub-pixel movement, yielding in effect smaller sub-pixels.

FIG. 8 illustrates an exemplary 2-dimensional half-pixel movements resulting in a pixel being divided into four effective smaller sub-"pixels" 260. An exemplary pixel 250 depicted by the heavy solid line is shown to be shifted with respect to the image (either by moving the target or the detector) in half-pixel steps to yield pixel positions 252 (heavy long dashed line), 254 (heavy short dashed line), and 256 (heavy dash-dot line). Such overlapping step movements yield an overlapping regions that are ¼ size of the pixel 250, and referred to as effective sub-pixels 260.

In one aspect, combination of signals from overlapping pixels at a given sub-pixel region approximates the "output" of that sub-pixel, thereby advantageously improving the resolution of the detector. As an example, a sub-pixel region 262 is where the pixel 250 overlaps with its shifted positions 252, 254, and 256. Other sub-pixels about the sub-pixel 262 overlap with the pixel 250 in its various positions and its neighboring pixels (not shown).

Approximating the sub-pixel's output may be achieved in a number of ways. One possible method is to sum the contributions of signals of the overlapping pixels. For the sub-pixel 262, the overlapping pixels' signals comprise the signals from the pixel 250 at its four positions. Thus, the sub-pixel 262 output may be approximated as $$I = \frac{\sum_{i=1}^{4} d_i a_i w_i}{W} \quad (1)$$

where $$W = \sum_{i=1}^{4} a_i w_i \quad (2)$$

represents normalization factor, $d_i$ represents i-th pixel (or in this case, the pixel signal at the i-th position), $a_i$ represents the fraction of the i-th pixel overlapping with the sub-pixel, and $w_i$ represents a user defined weight parameter; the four positions of the pixel are represented as i=1 to 4. In the particular example depicted in FIG. 8, $a_i$=¼ for all four positions. If the pixel 250 is exposed for substantially same duration at each position, each position "frame" may be given equal weight; such weight may be assigned, for example, 1, to yield a sub-pixel normalization (weight) W to be 1. In this simple example, the sub-pixel 262 output would then be I=¼×($d_1$+$d_2$+$d_3$+$d_4$) which is simply the average of the pixel 250 signals at the four positions.

Figure 9:
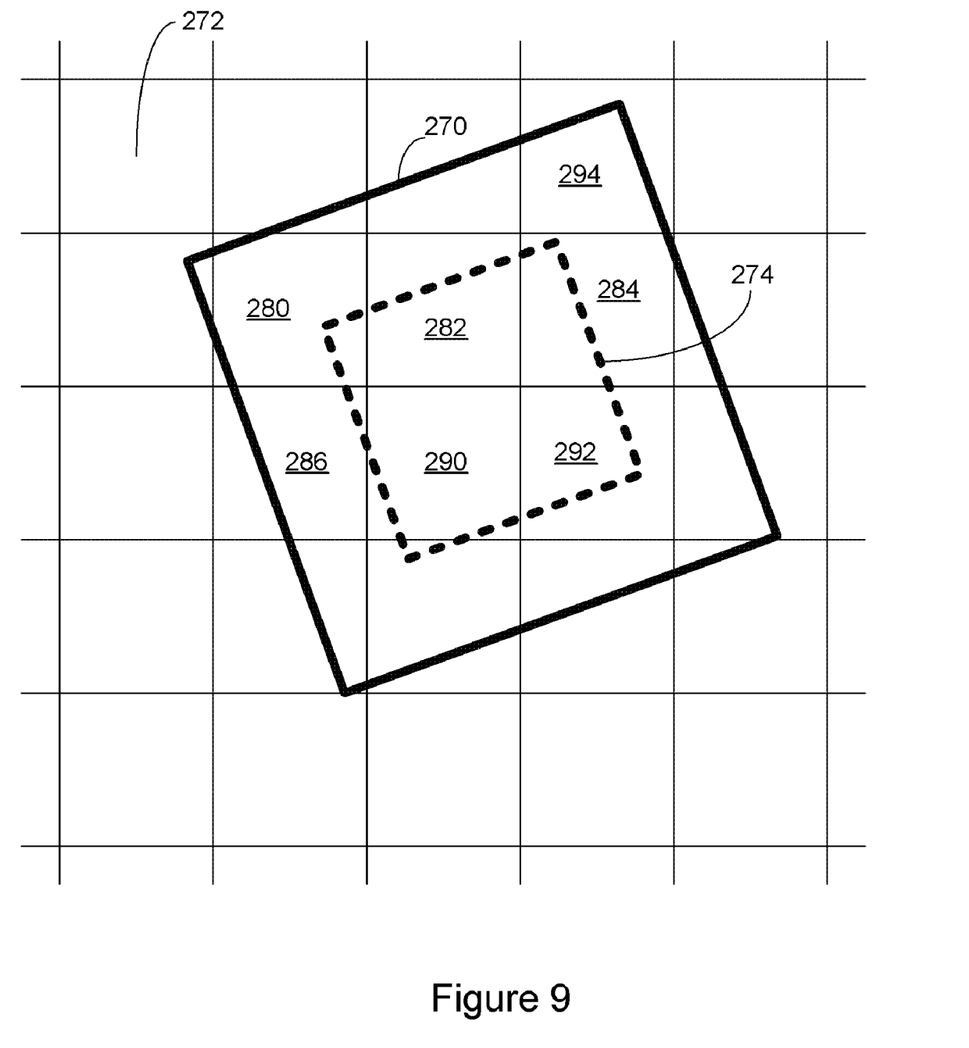
FIG. 9 illustrates a generalized sub-pixel movement and the mapping from a pixel space to a sub-pixel space.

It will be appreciated that foregoing description of approximating the sub-pixel output in reference to FIG. 8, and assignment of the associated parameters, are intended to be exemplary only for descriptive purpose. FIG. 9 illustrates a more general case where selected relative movements between the target and the detector result in a pixel 270 being mapped onto an array of effective sub-pixels 272. Equations 1 and 2 may then be generalized to $$I = \frac{\sum_i d_i a_i w_i}{W} \quad (3)$$

and $$W = \sum_i a_i w_i \quad (4)$$

where the index covers all the pixels that overlap with a given sub-pixel. So for example, sub-pixel 286 overlaps with pixel 270 and its adjacent pixel (not shown).

As is generally known, the sub-pixel dimensions may be such that the pixel covers a relatively large number of sub-pixels. Such situation may arise, for example, when the image size-dictated sub-pixel size (for example, the previously described 2–3 elements for FWHM) is substantially smaller than the physical dimensions of the pixels. In such situations, direct mapping of the pixels to the substantially smaller sub-pixels may not yield appreciable improvement in resolution.

One known technique of overcoming such situation comprises artificially shrinking the size of the pixel such that, when mapped onto the sub-pixel space, the shrunk pixel covers a smaller number of sub-pixels. The amount of shrinking depends partly on the pixel size and the image size. In FIG. 9, an exemplary shrunk pixel 274 maps onto parts of sub-pixels 280, 282, 284, 286, 290, and 292. Some sub-pixels may be excluded from coverage by the mapped shrunk pixel. For example, sub-pixel 294, which would be covered by the pixel 270 and two other neighboring pixels (not shown), is excluded from the shrunk pixel 274 coverage. The foregoing mapping method alters the overlap parameters $a_i$ (unless a sub-pixel is substantially completely within the shrunk pixel coverage), and may also alter the user defined weight parameter $w_i$. Such mapping technique have been shown to facilitate improvement of the resolution of the combined image.

In certain sub-pixel mapping applications, the mapping equation 3 described above may be modified to include a surface intensity term $s^2$ such that $$I = \frac{\sum_i d_i a_i w_i s^2}{W} \quad (5)$$

may provide an improved sub-pixel output approximation. Such technique is disclosed in a paper authored by A. Fruchter and R. Hook, and titled "Drizzle: A Method for the Linear Reconstruction of Undersampled Images," Publication of the Astronomical Society of the Pacific, 114–152, February 2002.

It will be appreciated that the present teachings may be implemented in any of the aforementioned mapping techniques, either independently or in combination. Furthermore, other similar mapping techniques may also be implemented to map pixel signals to sub-pixel space to improve the effective resolution without departing from the spirit of the present teachings.

Figure 10:
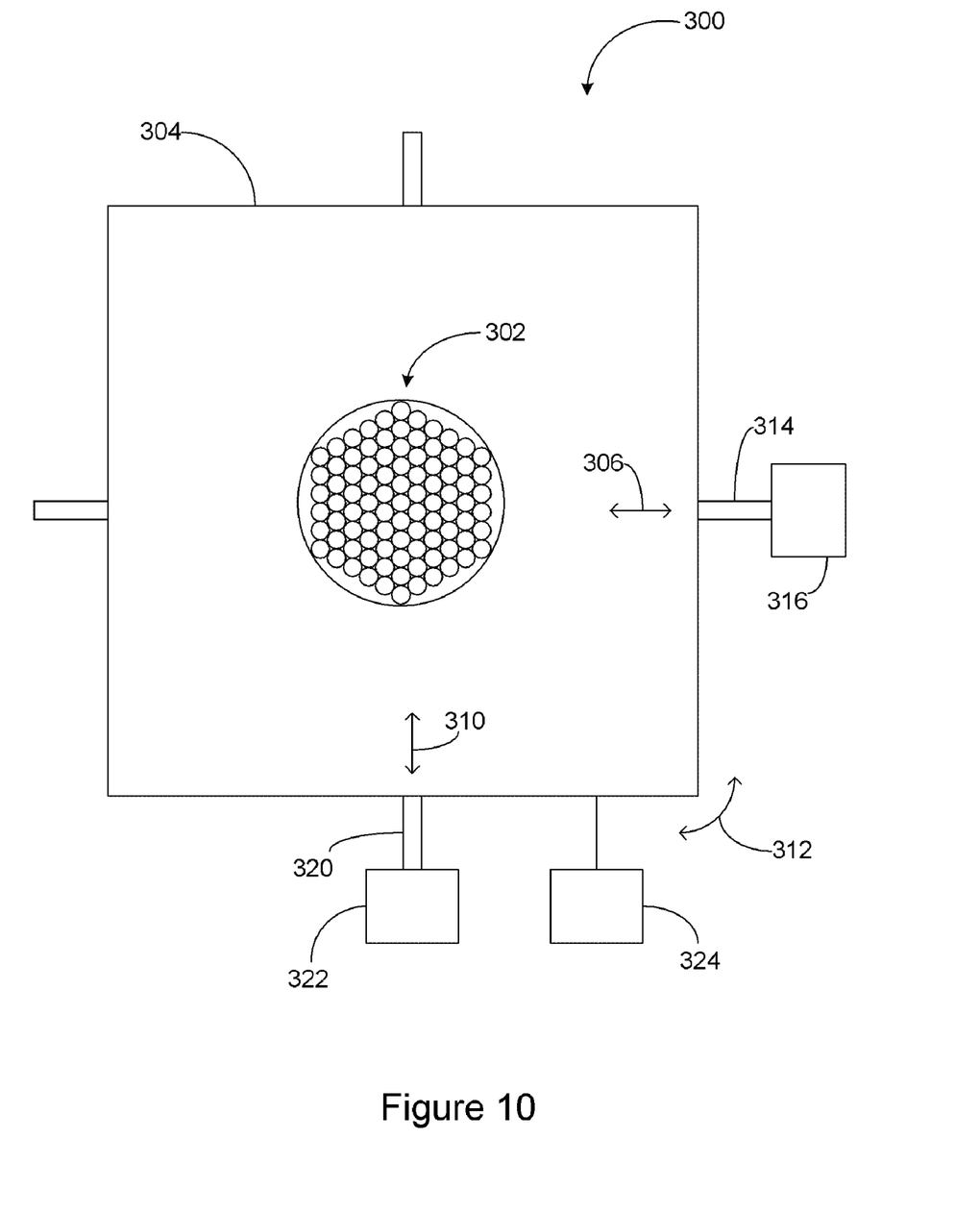
FIG. 10 illustrates one possible embodiment of a stage assembly that allows the biological sample platform to move relative to the segmented detector.

In certain embodiments, as illustrated in FIG. 10, various possible pixel-to-sub-pixel mapping techniques described above may be achieved by a stage assembly 300 having a stage 304 adapted to receive a biological sample platform 302. The stage assembly 300 further comprises a first drive member 314 coupled to a first actuator 316 so as to allow the stage 304 to move along a first direction 306. The stage assembly 300 further comprises a second drive member 320 coupled to a second actuator 322 so as to allow the stage 304 to move along a second direction 310. The stage 304 moving along the first and second directions 306, 310 can provide the relative motion between the sample platform 302 and the segmented detector (not shown). Preferably, the motion of the stage 304 is precise enough such that position error associated with the stage motion is less than the sub-pixel dimension.

In one exemplary biological analysis application, a sample platform comprises an array of fibers whose tips are treated so as to attract particular types of fragments. In one embodiment, each fiber's diameter is approximately 50 μm, and that diameter represents the feature size to be resolved. In one embodiment, a CCD associated with such a feature size has a pixel size of approximately 21 μm. Thus to resolve such an exemplary feature size, an exemplary sub-pixel movements in half-pixel steps could yield a well sampled measurement as described above (where two or more elements covering FWHM is generally considered to be representative of being well sampled).

It will be appreciated that the various sub-pixel movement techniques and the associated output combinations can be particularly suitable in biological analysis systems that have a pixel size that is greater than some selected value with respect to the dimension of a feature being measured. For example, a pixel size that is greater than ⅓ the feature size may be close to being categorized as an undersampling detector. Thus, such a pixel/feature size ratio may provide one possible boundary of analysis situations that may benefit from utilizing the sub-pixel movement and image combination described above.

In certain embodiments, the stage assembly 300 may further comprise a rotational movement mechanism 324 that allows rotational motion 312 of the stage 304. Such rotational motion may allow the generalized pixel to sub-pixel mapping described above in reference to FIGS. 7 and 9.

In FIG. 10, the relative motion between the sample platform and the detector is achieved by the motion of the stage. It will be appreciated that the relative motion between the sample platform and the detector may also be achieved by moving the detector relative to the platform, or by moving both the stage and the detector in some combination. In certain embodiments, movement of the stage may be more practical. In other embodiments, it may be optically advantageous to move the detector with respect to the image of the sample platform (i.e., with respect to the stage). Thus, it will be appreciated that various possible relative movements could be implemented without departing from the spirit of the present teachings.

Although the above-disclosed embodiments of the present invention have shown, described, and pointed out the fundamental novel features of the invention as applied to the above-disclosed embodiments, it should be understood that various omissions, substitutions, and changes in the form of the detail of the devices, systems, and/or methods illustrated may be made by those skilled in the art without departing from the scope of the present invention. Consequently, the scope of the invention should not be limited to the foregoing description, but should be defined by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A system for detecting one or more signals from an array of samples, the system comprising:
    a platform that supports the array of samples;
    a segmented detector configured to receive at least a portion of one or more signals associated with at least some of the array of samples to thereby form an optical image representative of the at least some of the array of samples;
    a movement mechanism that provides a relative movement between the platform and the segmented detector, the relative movement providing a lateral movement of the optical image in one or more sub-pixel sized steps; and
    a processor configured so as to facilitate the one or more sub-pixel sized steps to yield a plurality of optical images that are detected by the segmented detector to thereby allow combination of the plurality of optical images to yield a combined image.

2. The system of claim 1, wherein the movement mechanism comprises a movable stage coupled to the platform and wherein the movable stage is configured to move such that the image moves laterally with respect to an optical axis at the segmented detector and wherein the movable stage is capable of movements that cause the lateral movements of the image at a sub-pixel level.

3. The system of claim 2, wherein the pixel of the segmented detector has a generally square active area and wherein two perpendicular sides of the square area are respectively generally parallel to X and Y axes of a two dimensional detector coordinate system and wherein the sub-pixel movements of the image comprises sub-pixel movements along the X and Y axes.

4. The system of claim 3, wherein the magnitude of each sub-pixel movement along the X and Y axes is approximately an integer fraction of the side dimension of the square area.

5. The system of claim 4, wherein each sub-pixel movement magnitude is approximately ½ of the side dimension of the square area.

6. The system of claim 4, wherein each sub-pixel movement magnitude is approximately ⅓ of the side dimension of the square area.

7. The system of claim 1, wherein the platform comprises a bundle of fibers having their tips arranged generally in a planar manner wherein the tips of the fibers form a probe array that accommodates the array of samples and wherein the diameter of each fiber defines a feature size to be resolved by the segmented detector.

8. The system of claim 7, wherein the segmented detector comprises a CCD having a plurality of pixels shaped generally as squares.

9. The system of claim 8, wherein the pixel square is dimensioned such that the side of the pixel square is greater than approximately ⅓ of the diameter of the fiber.

10. The system of claim 9, wherein the pixel square side is approximately 21 µm long and the fiber diameter is approximately 50 µm.

11. The system of claim 1, wherein the sub-pixel sized shifts of the image relative to the segmented detector allows the processor to estimate what a sub-pixel sized element might output based on the combination of the associated pixels that overlap with the location of the sub-pixel sized element.

12. The system of claim 11, wherein the sub-pixel sized element is dimensioned according to the magnitudes of the sub-pixel sized shifts.

13. The system of claim 12, wherein the estimate of the sub-pixel element's output is expressed as $$I = \frac{\sum_i d_i a_i w_i}{W},$$

where $$W = \sum_i a_i w_i$$

and wherein $d_i$ represents the pixel output at the i-th position, $a_i$ represents the overlap fraction of the pixel at the i-th position with the sub-pixel element, and $w_i$ represents a weight parameter associated with the i-th position of the pixel.

14. The system of claim 13, wherein the weight parameter $a_i$ associated with the i-th position of the pixel is user defined.

15. The system of claim 14, wherein the weight parameter $a_i$ is assigned a constant value of 1/N where N is the number of pixel positions that overlap with the sub-pixel element.

16. A method for imaging an array of samples using a segmented detector, the method comprising:
    positioning the segmented detector relative to the array of samples such that an image of the array of samples is formed substantially at the segmented detector to thereby allow formation of data representative of the image of the array of samples;
    inducing one or more relative motions between the image of the array of samples and the segmented detector to thereby allow formation of a plurality of images of the array of samples; and
    combining data corresponding to the plurality of images of the array of samples to yield a combined image of the sample array.

17. The method of claim 16, wherein inducing the plurality of relative motions comprises causing the array of samples to move such that the image of the array of samples moves laterally with respect to an optical axis of the segmented detector.

18. The method of claim 17, wherein the movement of the array of samples causes the image to move by a step that is less than the dimension of a pixel of the segmented detector.

19. The method of claim 18, wherein the image movement step is an integer fraction of the pixel dimension.

20. The method of claim 19, wherein the pixel of the segmented detector has a generally square active area and wherein two perpendicular sides of the square area are respectively generally parallel to X and Y axes of a two dimensional detector coordinate system and wherein the image movement steps are along the X and Y axes.

21. The method of claim 16, wherein combining the data comprises combining outputs of pixels that overlap with a selected area on the segmented detector when the pixels are at the plurality of relative positions with respect to the image.

22. The method of claim 21, wherein the selected area comprises an area that has sub-pixel dimensions.

23. The method of claim 22, wherein an output that could result from the sub-pixel sized selected area is estimated as $$I = \frac{\sum_i d_i a_i w_i}{W},$$

where $$W = \sum_i a_i w_i$$

and wherein $d_i$ represents the pixel output at the i-th position, $a_i$ represents the overlap fraction of the pixel at the i-th position with the selected area, and $w_i$ represents a weight parameter associated with the i-th position of the pixel.

24. The method of claim 23, wherein the weight parameter $a_i$ associated with the i-th position of the pixel is user defined.

25. The method of claim 24, wherein the weight parameter $a_i$ is assigned a constant value of 1/N where N is the number of pixel positions that overlap with the selected area.

* * * * *